(12) United States Patent
Tachizaki et al.

(10) Patent No.: US 8,974,425 B2
(45) Date of Patent: Mar. 10, 2015

(54) MALE MEMBER

(75) Inventors: Hitoshi Tachizaki, Hiroshima (JP);
Tadashi Okiyama, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 0 days.

(21) Appl. No.: 14/124,157

(22) PCT Filed: Apr. 26, 2012

(86) PCT No.: PCT/JP2012/061220
§ 371 (c)(1),
(2), (4) Date: Dec. 5, 2013

(87) PCT Pub. No.: WO2012/169295
PCT Pub. Date: Dec. 13, 2012

(65) Prior Publication Data
US 2014/0114292 A1   Apr. 24, 2014

(30) Foreign Application Priority Data
Jun. 8, 2011 (JP) .................. 2011-128166

(51) Int. Cl.
*A61M 5/14* (2006.01)
*A61M 39/10* (2006.01)
(Continued)

(52) U.S. Cl.
CPC ................ *A61M 39/10* (2013.01); *F16L 37/30* (2013.01); *A61M 2039/1027* (2013.01); *A61M 2039/1066* (2013.01); *A61M 2039/2433* (2013.01); *A61M 2039/2473* (2013.01); *Y10S 604/905* (2013.01)
USPC ............................ 604/256; 604/533; 604/905

(58) Field of Classification Search
CPC ... A61M 39/29; A61M 39/045; A61M 39/10; A61M 2039/267; A61M 2039/266; A61M 2039/1072; A61M 2039/1066

USPC ................... 128/912; 604/246, 256, 533, 905
See application file for complete search history.

(56) References Cited

U.S. PATENT DOCUMENTS 5,700,248 A * 12/1997 Lopez .......................... 604/249
6,468,251 B1  10/2002 Yamanaka et al.
(Continued)

FOREIGN PATENT DOCUMENTS

JP   2000-501963    2/2000
JP   2002-526179    8/2002
(Continued)

*Primary Examiner* — Nicholas Lucchesi
*Assistant Examiner* — Gerald Landry, II
(74) *Attorney, Agent, or Firm* — Hamre, Schumann, Mueller & Larson, P.C.

(57) ABSTRACT

A male member (1) includes a tubular member (10) and a cover (20) covering at least a tip (11) of the tubular member. A lateral hole (14) that communicates with a flow path (13) is formed in an outer peripheral surface of the tubular member. The cover includes an outer peripheral wall (21) that can be deformed elastically by compression and a head part (23) that is provided at one end of the outer peripheral wall. The head part includes an interior cavity (24) into which the tubular member is inserted, and a slit (25) is formed in an innermost part (24a) of the interior cavity. In a state where the outer peripheral wall is not deformed by compression, an inner peripheral surface of the interior cavity contacts closely with the outer peripheral surface of the tubular member so as to block the lateral hole, and the tip of the tubular member and the innermost part of the interior cavity are spaced apart from each other. Thereby, it is possible to reduce an amount of a liquid substance adhering to outer surfaces of the cover and a female member after separation from the female member.

6 Claims, 11 Drawing Sheets

(51) Int. Cl.
*F16L 37/30* (2006.01)
*A61M 39/24* (2006.01)

(56) References Cited

U.S. PATENT DOCUMENTS

| | | |
|---|---|---|
| 7,470,262 B2 | 12/2008 | Hiejima et al. |
| 2003/0032940 A1* | 2/2003 | Doyle .................. 604/533 |
| 2004/0122351 A1* | 6/2004 | Hamazaki .............. 604/27 |
| 2006/0264841 A1* | 11/2006 | Cote et al. .............. 604/247 |
| 2008/0190485 A1* | 8/2008 | Guala .................. 137/1 |
| 2011/0175347 A1 | 7/2011 | Okiyama |
| 2011/0178493 A1 | 7/2011 | Okiyama |
| 2011/0276035 A1* | 11/2011 | Fangrow et al. ......... 604/535 |
| 2011/0282302 A1* | 11/2011 | Lopez et al. ........... 604/247 |
| 2012/0016345 A1* | 1/2012 | Carter et al. ........... 604/533 |
| 2012/0232499 A1* | 9/2012 | Stout et al. ............ 604/256 |
| 2012/0302997 A1* | 11/2012 | Gardner et al. ......... 604/533 |

FOREIGN PATENT DOCUMENTS

| | | |
|---|---|---|
| JP | 3389983 | 3/2003 |
| JP | 2004-298618 | 10/2004 |
| JP | 2007-517631 | 7/2007 |
| JP | 4163975 | 10/2008 |
| JP | 2011-500103 | 1/2011 |
| WO | 97/21464 | 6/1997 |
| WO | 00/20070 | 4/2000 |
| WO | 2005/069832 | 8/2005 |
| WO | 2008/052140 | 5/2008 |
| WO | 2010/061742 | 6/2010 |
| WO | 2010/061743 | 6/2010 |

* cited by examiner

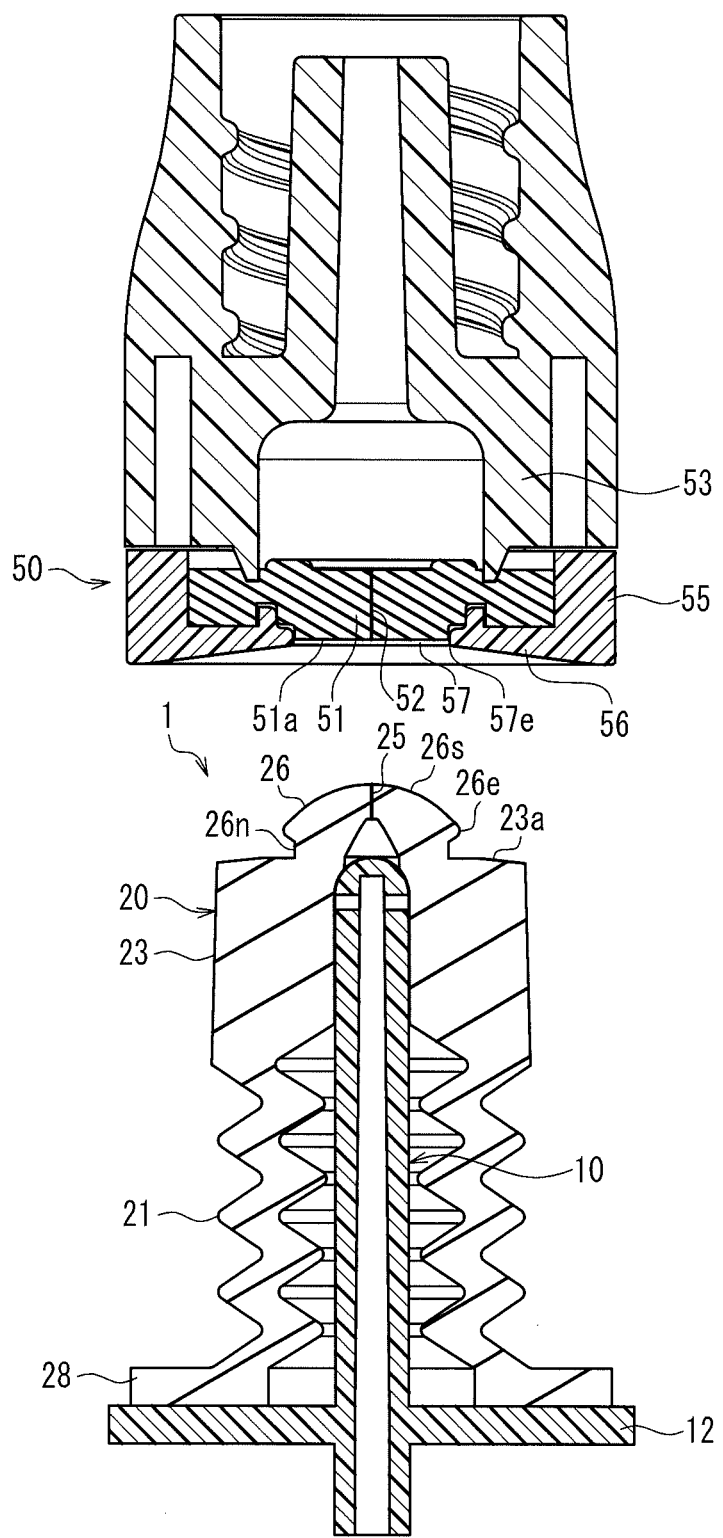
F I G. 4A

MALE MEMBER

TECHNICAL FIELD

The present invention relates to a male member that includes a tubular member in which a flow path for carrying a liquid substance is formed and a cover that covers at least a tip of the tubular member.

BACKGROUND ART

In the case of a liquid transfusion and a blood transfusion to a patient and extracorporeal circulation in surgery, a path (transport line) must be formed for transporting a liquid substance, such as a drug solution and blood. The transport line generally is formed by connecting vessels, various instruments, tubes, etc. As a method for connecting different members, there has been known a slip connection between a male luer as a male member and a needle-less port as a female member (for example, see Patent Documents 1, 2). The needle-less port includes a partition member (hereinafter, referred to as "septum") made of an elastic material such as rubber, with the middle formed with a linear slit (cut). By inserting a male luer (tubular body) to which no sharp metal needle such as an injection needle is attached into the slit of the septum, the needle-less port and the male luer can communicate with each other. The slit of the septum immediately closes when the male luer is removed from the needle-less port. Thus, the septum has resealability and the male luer can be inserted and removed repeatedly.

In the above-mentioned slip connection, since the slit of the septum immediately closes when the male luer is removed from the needle-less port, generally a liquid substance is less likely to leak from the needle-less port to which the male luer is not connected. However, since the male luer is exposed to the outside before insertion into and after removal from the needle-less port, there is a possibility that the liquid substance leaks from the male luer.

For reducing the possibility of the liquid substance leaking from the male luer that is not connected to the needle-less port, as shown in FIG. 7, there has been known a method for covering a male luer 110 with an expansible cover 120 (see Patent Documents 3, 4). The cover 120 includes an outer peripheral wall 121 having a substantially cylindrical shape, one end of which is blocked by a top plate 123. The male luer 110 has a cylindrical shape, and an opening 112 is formed at the tip for inflow and outflow of the liquid substance. A linear slit (cut) 125 is formed in the top plate 123 at a position facing the opening 112 of the male luer 110. A septum 151 of a needle-less port 150 is a disk-shaped member made of an elastic material such as rubber, with the middle formed with a linear slit (cut) 152. The septum 151 is sandwiched and fixed by a base body part 153 having a substantially circular cylindrical shape and a port cap 155.

As shown in FIG. 7, when the male luer 110 is not connected to the needle-less port 150, the top plate 123 of the cover 120 contacts closely with the opening 112 of the male luer 110 so as to block the opening 112. The slit 125 of the cover 120 is closed. From this state, when the male luer 110 is pushed into the needle-less port 150, the male luer 110 penetrates the slit 125 of the cover 120, and further penetrates the slit 152 of the septum 151, thereby being connected to the needle-less port 150. At this time, the outer peripheral wall 121 of the cover 120 is deformed by compression. Thereafter, when the male luer 110 is taken out from the needle-less port 150, the outer peripheral wall 121 of the cover 120 extends due to its elastic recoverability, thereby returning to the initial state.

As described above, by attaching the cover 120 on the male luer 110, in the state where the male luer 110 is not connected to the needle-less port 150 as shown in FIG. 7, the opening 112 of the male luer 110 can be blocked by the top plate 123 of the cover 120. Therefore, the possibility of the liquid substance leaking from the male luer 110 is low.

PRIOR ART DOCUMENTS

Patent Documents

Patent Document 1: JP 3389983
Patent Document 2: JP 4163975
Patent Document 3: WO/2010/061742 (FIGS. 7, 8)
Patent Document 4: WO/2010/061743 (FIGS. 10, 11)

DISCLOSURE OF INVENTION

Problem to be Solved by the Invention

However, in the configuration of FIG. 7, there is a problem that, when the male luer 110 is taken out from the needle-less port 150, the liquid substance remains on an outer surface 123a of the top plate 123 of the cover 120 and an outer surface 151a of the septum 151.

For example, if bacteria grow in the liquid substance remaining on the outer surface 123a of the top plate 123 of the cover 120 and the outer surface 151a of the septum 151, they may be mixed in a liquid-substance transport path when the male luer 110 is reconnected to the needle-less port 150 later.

Further, in the case where the liquid substance contains a drug that is designated as a powerful drug, such as one of the antineoplastic agents, and if the liquid substance remains on the outer surface 123a of the top plate 123 of the cover 120 and the outer surface 151a of the septum 151, there is a possibility that the liquid substance adheres to fingers of an operator, or the operator inhales a vapor of the liquid substance.

It is an object of the present invention in a male member provided with a cover that prevents a liquid substance leakage when unconnected to a female member, to reduce an amount of a liquid substance adhering to an outer surface of the cover and an outer surface of the female member after separation from the female member.

Means for Solving Problem

A male member of the present invention includes a tubular member in which a flow path for carrying a liquid substance is formed and a cover that covers at least a tip of the tubular member. A lateral hole that communicates with the flow path is formed in an outer peripheral surface of the tubular member. The cover includes an outer peripheral wall that can be deformed elastically by compression and a head part that is provided at one end of the outer peripheral wall. The head part includes an interior cavity into which the tip of the tubular member is inserted. A slit that penetrates the head part is formed in an innermost part of the interior cavity. In a state where the outer peripheral wall is not deformed by compression, an inner peripheral surface of the interior cavity of the head part contacts closely with the outer peripheral surface of the tubular member so as to block the lateral hole, and the tip of the tubular member and the innermost part of the interior cavity are spaced apart from each other. When the head part is displaced with respect to the tubular member so that the outer peripheral wall is deformed by compression, the tubular member penetrates the slit and the lateral hole is exposed from the head part.

Effect of the Invention

According to the present invention, in the state where the outer peripheral wall of the cover is not deformed by compression, since the inner peripheral surface of the interior cavity of the head part blocks the lateral hole of the tubular member, it is possible to prevent the liquid substance leakage from the male member when the male member is not connected to the female member.

Further, in the state where the outer peripheral wall of the cover is not deformed by compression, the tip of the tubular member and the innermost part of the interior cavity with the slit are spaced apart from each other. Therefore, in a space formed between the tip of the tubular member and the innermost part of the interior cavity in the process of separating the male member from the female member, it is possible to generate negative pressure in accordance with the increase in the capacity of the space. The negative pressure draws into the space the liquid substance remaining between the cover and the female member. Consequently, it is possible to reduce the amount of the liquid substance adhering to the outer surface of the cover and the outer surface of the female member after separation of the male member and the female member.

BRIEF DESCRIPTION OF DRAWINGS

FIG. 4A is a cross-sectional view of the male member and a needle-less port before connection according to one embodiment of the present invention.

DESCRIPTION OF THE INVENTION

Figure 7:
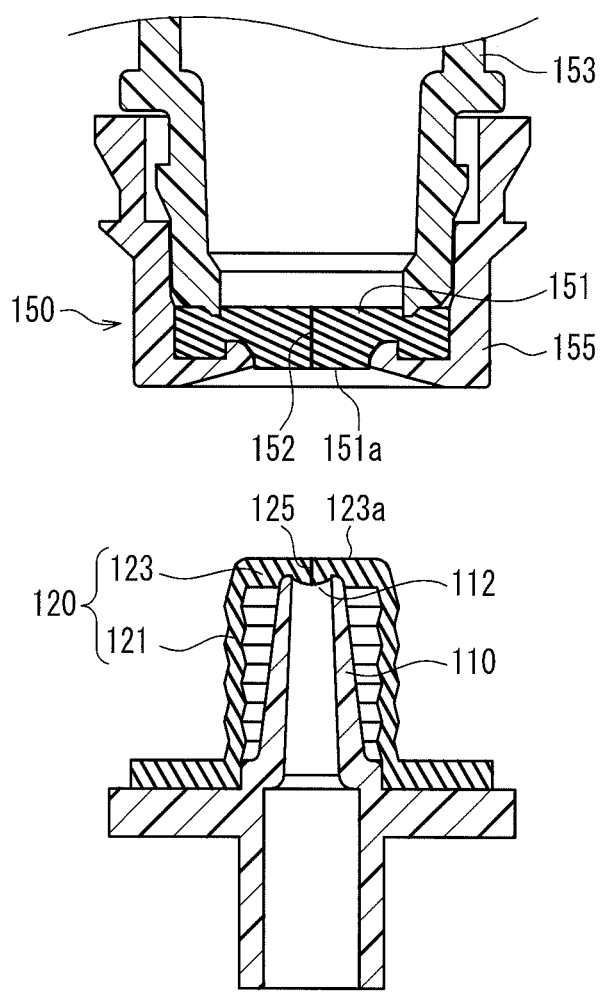
FIG. 7 is a cross-sectional view showing a conventional male luer equipped with a cover to be connected to a needle-less port.

In order to investigate the cause of the liquid substance remaining on the outer surface 123a of the top plate 123 of the cover 120 and the outer surface 151a of the septum 151 after removal of the male luer 110 from the needle-less port 150 in the case of using the conventional male luer 110 equipped with the cover 120 shown in FIG. 7, the inventors of the present invention observed using an X-ray CT how the septum 151 and the cover 120 were deformed from the connection to the separation of the male luer 110 with respect to the needle-less port 150. The following describes the detail.

FIGS. 8A to 8D are cross-sectional views sequentially showing states where the conventional male luer 110 equipped with the cover 120 is inserted into the needle-less port 150. The slit 152 in the septum 151 and the slit 125 in the top plate 123 of the cover 120 are formed along a direction perpendicular to the cross section of the drawings.

Figure 8A:
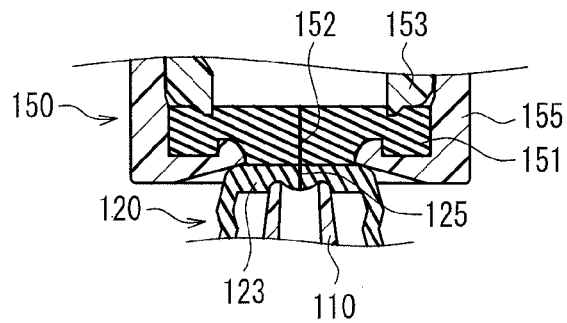
FIGS. 8A to 8D are cross-sectional views sequentially showing states where the conventional male luer equipped with the cover is inserted into the needle-less port.

FIG. 8A shows a state immediately before the connection between the male luer 110 and the needle-less port 150. The top plate 123 of the cover 120 attached to the male luer 110 contacts the port cap 155 of the needle-less port 150. From this state, the male luer 110 is pushed into the needle-less port 150.

Figure 8B:
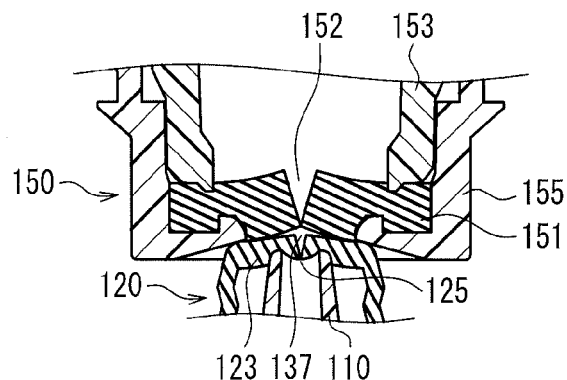

FIG. 8B shows a state where the top plate 123 of the cover 120 is deformed slightly toward the septum 151 by the male luer 110. The septum 151 also is deformed slightly by the deformed top plate 123. A little gap 137 is created between the top plate 123 and the septum 151. The slit 125 of the top plate 123 and the slit 152 of the septum 151 are not open yet.

Figure 8C:
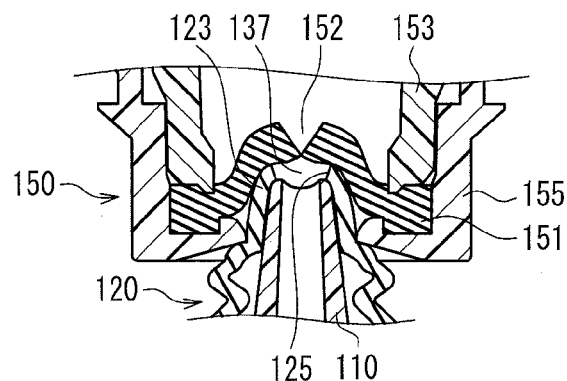

When the male luer 110 is pushed further into the needle-less port 150, the slit 125 of the top plate 123 of the cover 120 opens as shown in FIG. 8C. The top plate 123 is stretched by the male luer 110 and enters an opening of the port cap 155. Thus, the septum 151 also is deformed and the gap 137 becomes larger. Incidentally, the slit 152 of the septum 151 is not open yet.

Figure 8D:
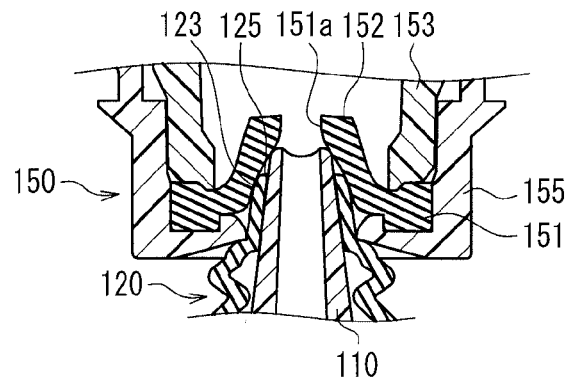

FIG. 8D shows a state where the connection between the male luer 110 and the needle-less port 150 is completed. The deformation of the top plate 123 is increased further, and the male luer 110 penetrates the slit 125 of the top plate 123. A tip of the male luer 110 presses the outer surface 151a of the septum 151, thereby significantly bending and stretching the septum 151 and opening the slit 152. In this manner, the male luer 110 and the needle-less port 150 communicate with each other.

Then, a liquid substance is caused to flow between the male luer 110 and the needle-less port 150. The outer surface 151a of the septum 151 constitutes part of a flow-path wall where a liquid substance flows.

Next, from the state of FIG. 8D, the male luer 110 is pulled out from the needle-less port 150. Before the pullout, the flow of the liquid substance between the male luer 110 and the needle-less port 150 is stopped. Generally, even after the stoppage of the flow of the liquid substance, the liquid substance is filled in the male luer 110 and the needle-less port 150. The pullout of the male luer 110 from the needle-less port 150 proceeds from FIG. 8D to FIG. 8A, which is in a reverse order to that described above.

When the male luer 110 retreats from the needle-less port 150 from the state of FIG. 8D, the slit 152 of the septum 151 closes in the state of FIG. 8C, and subsequently the slit 125 of the top plate 123 closes in the state of FIG. 8B. Therefore, the liquid substance that is located in the vicinity of the outer surface 151a of the septum 151 in FIG. 8D is trapped in the gap 137. Thereafter, when the male luer 110 is pulled out from the needle-less port 150, and the cover 120 and the septum 151 are separated, the liquid substance in the gap 137 remains on the outer surface 123a of the top plate 123 of the cover 120 and the outer surface 151a of the septum 151 as described above.

The inventors of the present invention have found that, by properly designing the shape of the tubular member (e.g., male luer) and the shape of the cover that covers at least the tip of the tubular member based on the above-mentioned finding, it is possible to reduce the amount of the liquid substance adhering to the outer surface of the cover and the outer surface of the female member after separation of the tubular member from the female member (e.g., needle-less port), and thus have accomplished the present invention.

Specifically, the male member of the present invention includes a tubular member in which a flow path for carrying a liquid substance is formed and a cover that covers at least a tip of the tubular member. A lateral hole that communicates with the flow path is formed in an outer peripheral surface of the tubular member. The cover includes an outer peripheral wall that can be deformed elastically by compression and a head part that is provided at one end of the outer peripheral wall. The head part includes an interior cavity into which the tip of the tubular member is inserted. A slit that penetrates the head part is formed in an innermost part of the interior cavity. In a state where the outer peripheral wall is not deformed by compression, an inner peripheral surface of the interior cavity of the head part contacts closely with the outer peripheral surface of the tubular member so as to block the lateral hole, and the tip of the tubular member and the innermost part of the interior cavity are spaced apart from each other. When the head part is displaced with respect to the tubular member so that the outer peripheral wall is deformed by compression, the tubular member penetrates the slit and the lateral hole is exposed from the head part.

It is preferable that a protruding top part is formed at a tip of the head part, and the slit is formed in the top part. Thereby, it is possible to further reduce the amount of the liquid substance adhering to the outer surface of the cover and the outer surface of the female member after separation of the male member and the female member.

It is preferable that a surface of the top part on a side facing a female member includes a convex surface that protrudes toward the female member. Thereby, it is possible to further reduce the amount of the liquid substance adhering to the outer surface of the cover and the outer surface of the female member after separation of the male member and the female member.

It is preferable that the convex surface includes a spherical surface, a circular conical surface, or a circular truncated conical surface. Thereby, it is possible to simplify the shape of the outer surface of the top part.

It is preferable that an engagement shape that can be engaged with the female member is formed in the head part. Thereby, it is possible to reduce further the amount of the liquid substance adhering to the outer surface of the cover and the outer surface of the female member after separation of the male member and the female member. Further, it is possible to extend reliably the outer peripheral wall of the cover to the initial state in the process of separating the male member from the female member. The engagement shape can be formed in the top part.

It is preferable that, in the state where the outer peripheral wall is not deformed by compression, an airtight space is formed between the tip of the tubular member and the innermost part of the interior cavity. Thereby, it is possible to generate a larger negative pressure in the space in the process of separating the male member from the female member. Therefore, it is possible to reduce further the amount of the liquid substance adhering to the outer surface of the cover and the outer surface of the female member after separation of the male member and the female member.

The following describes the present invention in detail while referring to a preferred embodiment. Needless to say, the present invention is not limited to the following embodiment. For convenience of explanation, the respective drawings referred to herein are simplified drawings showing exclusively principal members necessary for explaining the present invention, among constituent members of the embodiment of the present invention. The present invention therefore possibly includes arbitrary constituent members not shown in the following respective drawings. Besides, dimensions of the members shown in the following respective drawings do not faithfully represent the actual dimensions of the constituent members and the actual dimension ratios of the members.

Figure 1:
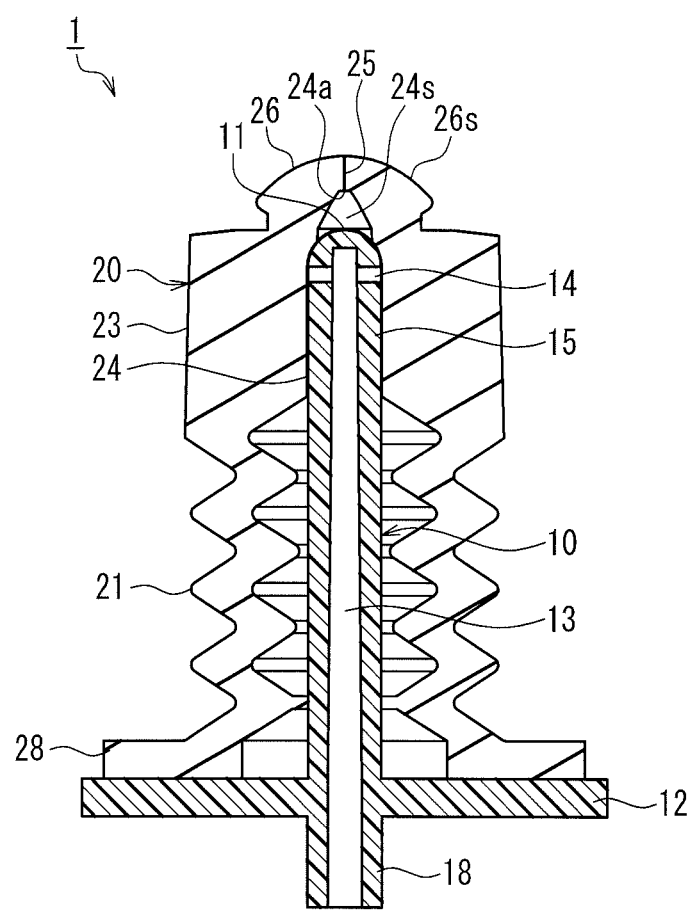
FIG. 1 is a cross-sectional view showing a schematic configuration of a male member according to one embodiment of the present invention.

FIG. 1 is a cross-sectional view showing a schematic configuration of a male member 1 according to one embodiment of the present invention. The male member 1 includes a tubular member 10 and a cover 20 that covers at least a tip 11 of the tubular member 10. For convenience of the following explanation, the upper side and lower side of FIG. 1 are referred to as "upper side" and "lower side" of the male member 1, respectively. However, they do not necessarily indicate the upper and lower sides of the male member 1 in actual use.

The tubular member 10 has a cylindrical shape in which a flow path 13 for carrying a liquid substance is formed along a longitudinal direction of the tubular member 10. An outer peripheral surface of the tubular member 10 preferably is a circular cylindrical surface whose outer diameter is uniform along the longitudinal direction of the tubular member 10, or a tapered surface whose outer diameter decreases from a base 12 toward the tip 11. A lateral hole 14 is formed in the vicinity of the tip 11 of the outer peripheral surface of the tubular member 10. The lateral hole 14 is a through hole that communicates with the flow path 13 and that penetrates an outer peripheral wall of the tubular member 10 in a direction substantially orthogonal to the longitudinal direction of the tubular member 10. In the present embodiment, although a pair of the lateral holes 14 is formed along a diameter direction of the tubular member 10, the number of the lateral hole 14 is not limited to this and may be one or three or more. The liquid substance flows out or into the flow path 13 via the lateral hole 14. In the conventional male luer 110 shown in FIG. 7, the opening 112 is formed at its tip. However, at the tip 11 of the tubular member 10 of the present embodiment, an opening (or a through hole) that communicates with the flow path 13 is not formed. On the side of the base 12 opposite to the tubular member 10, a cylindrical part 18 having a substantially circular cylindrical shape that communicates with the tubular member 10 is formed. For transporting the liquid substance to the tubular member 10, a pliable tube (not shown) is connected to the cylindrical part 18, for example. The tubular member 10 preferably is made of a hard material that can be regarded as a substantially rigid body. Specifically, the tubular member 10 can be made together with the base 12 and the cylindrical part 18 by an intergral molding method or the like using a resin material such as polyacetal and polycarbonate.

Figure 2A:
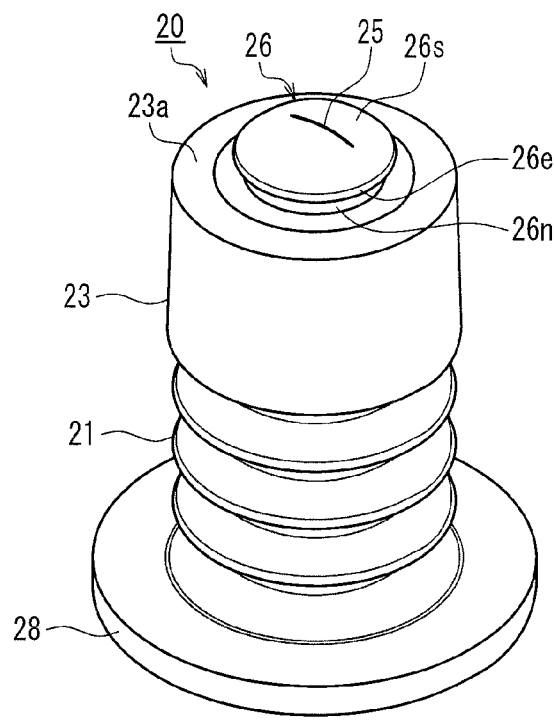
FIG. 2A is a perspective view of a cover constituting the male member according to one embodiment of the present invention seen from above.
Figure 2B:
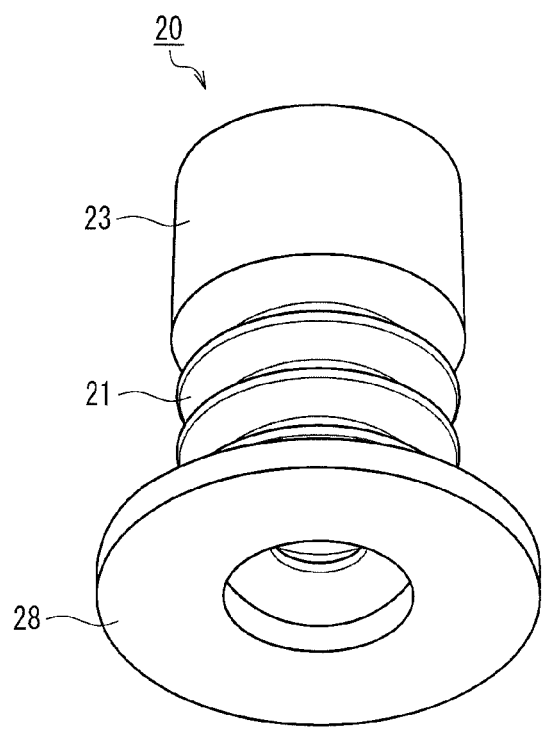
FIG. 2B is a perspective view thereof seen from below.
Figure 3A:
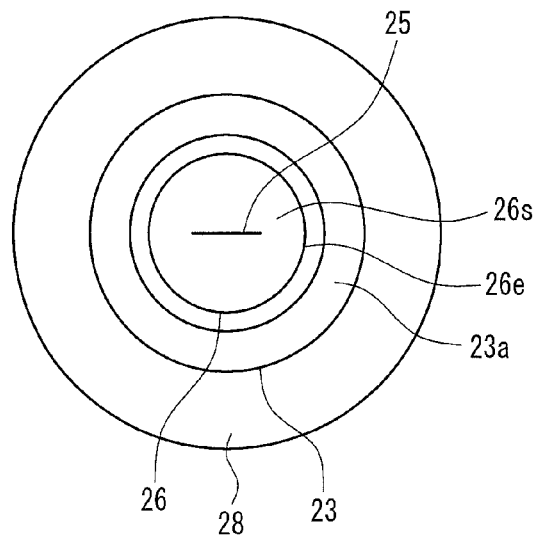
FIG. 3A is a top view of the cover constituting the male member according to one embodiment of the present invention.
Figure 3B:
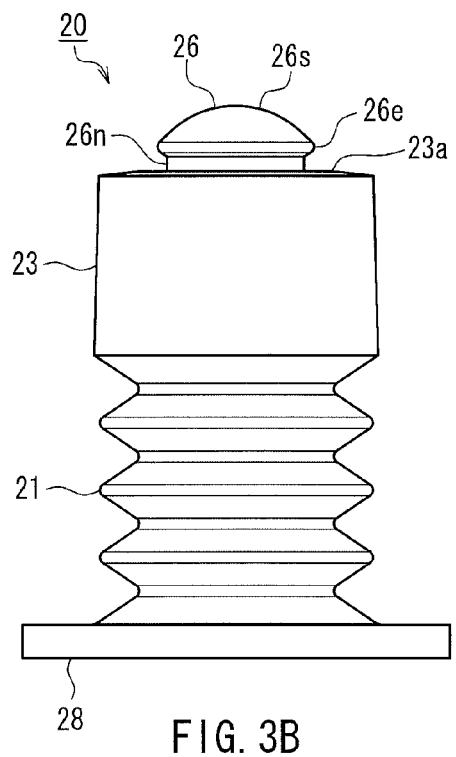
FIG. 3B is a side view thereof.
Figure 3C:
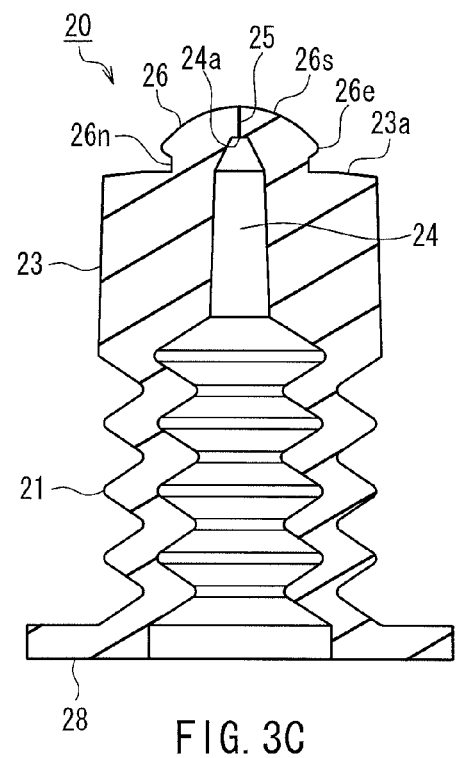
FIG. 3C is a cross-sectional view thereof taken along a vertical direction.

FIG. 2A is a perspective view of the cover 20 seen from above, and FIG. 2B is a perspective view thereof seen from below. FIG. 3A is a top view thereof, FIG. 3B is a side view thereof, and FIG. 3C is a cross-sectional view thereof taken along the vertical direction.

The cover 20 includes an outer peripheral wall 21 having a substantially cylindrical shape, a head part 23 provided at an upper end of the outer peripheral wall 21, and a ring-shaped base part 28 provided at a lower end of the outer peripheral wall 21. A body of the cover 20 can be made integrally using a material with flexibility (pliability) (e.g., silicone rubber, isoprene rubber).

The outer peripheral wall 21 can be deformed elastically by compression so that the dimension decreases in the vertical direction. For realizing this, in the present embodiment, the outer peripheral wall 21 has a bellows shape whose outer diameter and inner diameter changes regularly in the vertical direction within a given range. Although in the present embodiment the cross-sectional shape of the outer peripheral wall 21 taken along the horizontal direction is circular, it may have any shape such as a polygon, e.g., tetragon and hexagon.

In the head part 23, an interior cavity 24 that communicates with an internal space of the outer peripheral wall 21 is formed. An inner peripheral surface of the interior cavity 24 is a circular cylindrical surface, or a circular conical surface (tapered surface) whose inner diameter decreases with distance from the outer peripheral wall 21. In an innermost part 24a of the interior cavity 24, a slit 25 that vertically penetrates the head part 23 is formed. As shown in FIG. 3A, the slit 25 is a linear cut having a "–" (minus) shape seen from above. In a normal state where the tubular member 10 does not penetrate the slit 25, the opposing edges forming the slit 25 preferably are in contact with each other.

On an upper surface 23a of the head part 23, a top part 26 that protrudes from the upper surface 23a is formed. A tip of the top part 26 is a convex surface 26s that curves smoothly in a dome shape, e.g., a spherical surface. A neck 26n is formed between the upper surface 23a of the head part 23 and the convex surface 26s. A portion where an outer diameter of the convex surface 26s is maximum and that is adjacent to the neck 26n is called a top edge 26e. An outer diameter of the neck 26n is smaller than an outer diameter of the top edge 26e. When seen from above (see FIG. 3A), the outer diameter of the top edge 26e is a circle, and the slit 25 is formed to pass through the center of the circle.

As shown in FIG. 1, the tubular member 10 is inserted into the cover 20 from the base part 28 side, and the base part 28 of the cover 20 is fixed to the base 12 of the tubular member 10. A method for fixing the base part 28 to the base 12 is not limited particularly, and any method such as adhesion, fusion, engagement, fit and the like can be used. In order to align the tubular member 10 with the cover 20 accurately, the base 12 and the base part 28 may include fitting shapes that fit with each other.

When the cover 20 is attached to the tubular member 10, the tip 11 of the tubular member 10 is inserted into the interior cavity 24 of the head part 23 of the cover 20. In the state shown in FIG. 1 where the outer peripheral wall 21 of the cover 20 is not deformed by compression, a portion of the tubular member 10 that is inserted in the interior cavity 24 is called a tip region 15. The lateral hole 14 is formed in the tip region 15. An outer diameter of the tip region 15 is the same as or slightly larger than an inner diameter of the interior cavity 24. Therefore, the inner peripheral surface of the interior cavity 24 contacts closely with the outer peripheral surface of the tubular member 10, thereby blocking the lateral hole 14. Further, the tip 11 of the tubular member 10 and the innermost part 24a of the interior cavity 24 are spaced apart from each other, whereby a space 24s is formed therebetween. The tip 11 of the tubular member 10 and the slit 25 face each other, with the space 24s therebetween. Preferably, the slit 25 is sealed. Hence, preferably, the space 24s is sealed air-tightly.

The following describes a slip connection between the male member 1 of the present embodiment and a needle-less port as a female member, and separation therefrom.

FIG. 4A is a cross-sectional view of the male member 1 and a needle-less port 50 before connection. Similarly to the needle-less port 150 shown in FIG. 7, the needle-less port 50 includes a septum 51. The septum 51 is a disk-shaped partition member made of an elastic material such as rubber, with the middle formed with a linear slit (cut) 52. The septum 51 is sandwiched and fixed by a base body part 53 having a substantially circular cylindrical shape and a port cap 55. The port cap 55 includes a pressing plate 56 on the side facing the male member 1. A round opening 57 is formed in the middle of the pressing plate 56. The slit 52 of the septum 51 is exposed in the opening 57.

Figure 4B:
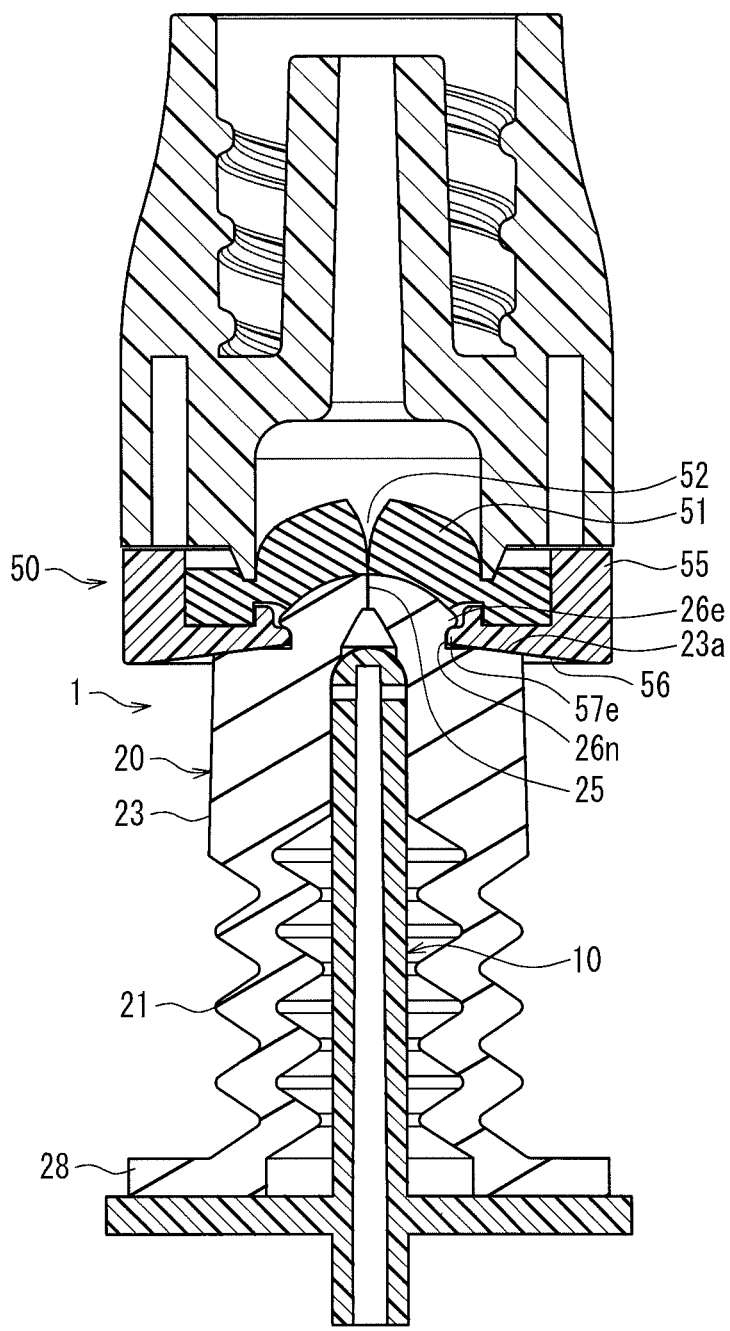
FIG. 4B is a cross-sectional view of the male member and the needle-less port during connection according to one embodiment of the present invention.

As shown in FIG. 4A, the male member 1 and the needle-less port 50 are brought to face each other, and the male member 1 is pressed into the needle-less port 50. First, the convex surface 26s of the top part 26 of the male member 1 contacts an outer surface 51a of the septum 51, and both contact closely with each other. The top part 26 pressed by the tubular member 10 enters the opening 57 of the pressing plate 56 while elastically deforming the septum 51. Finally, as shown in FIG. 4B, the top edge 26e of the top part 26 passes an opening edge 57e of the opening 57 of the pressing plate 56 and the opening edge 57e fits in the neck 26n, whereby the top edge 26e and the opening edge 57e are engaged with each other. Substantially at the same time with this, the upper surface 23a of the head part 23 of the male member 1 contacts the pressing plate 56, whereby the movement of the head part 23 with respect to the needle-less port 50 side is restricted. Therefore, when the male member 1 is pushed further into the needle-less port 50, the tip 11 of the tubular member 10 enters and penetrates the slit 25 of the head part 23, and further penetrates the slit 52 of the septum 51. In this process, the outer peripheral wall 21 of the cover 20 is deformed elastically by compression in the vertical direction.

Figure 4C:
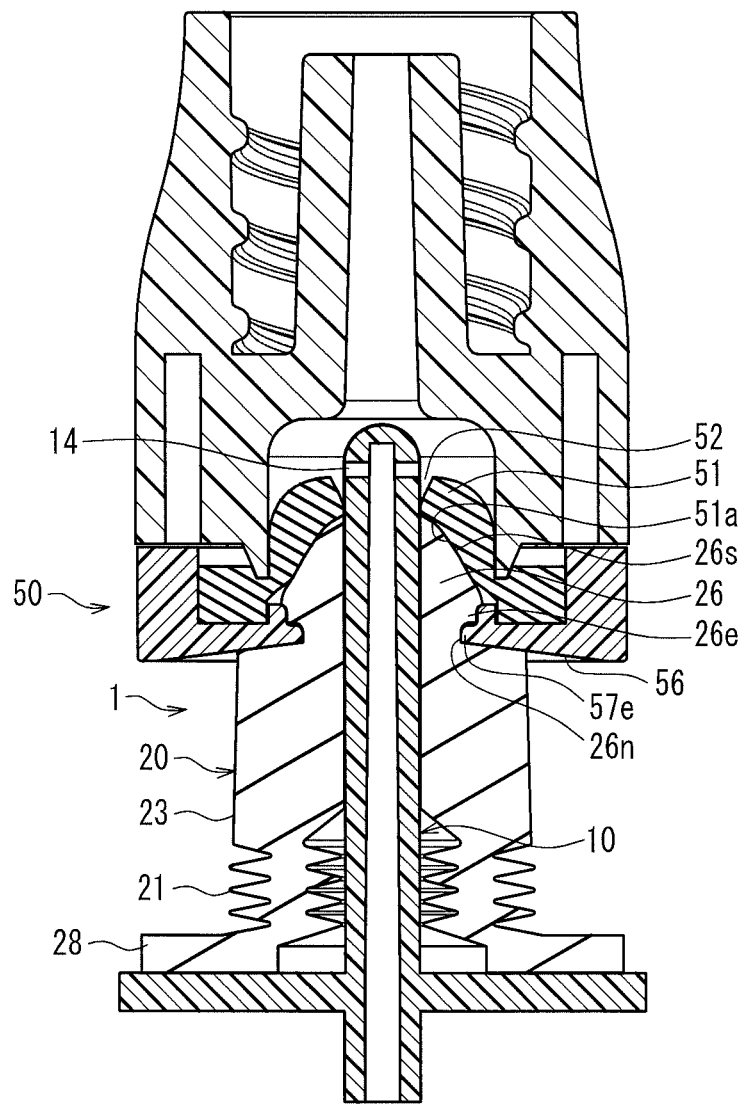
FIG. 4C is a cross-sectional view of the male member and the needle-less port at completion of connection according to one embodiment of the present invention.

In this manner, as shown in FIG. 4C, the slip connection can be established between the male member 1 and the needle-less port 50. The insertion of the top part 26 into the opening 57 of the pressing plate 56 deforms the septum 51 elastically. The convex surface 26s of the top part 26 contacts closely with the outer surface 51a of the septum 51. The top edge 26e of the top part 26 is engaged with the opening edge 57e of the pressing plate 56. The tubular member 10 penetrates the slit 25 of the head part 23 and the slit 52 of the septum 51 in this order. An edge of the slit 52 surrounds and contacts closely with the outer peripheral surface of the tubular member 10. The lateral hole 14 of the tubular member 10 is located on a backside of the septum 51 (on the side opposite to the top part 26), and the male member 1 and the needle-less port 50 communicate with each other via the lateral hole 14. Therefore, in this state, the liquid substance can flow between the male member 1 and the needle-less port 50. Since the outer surface 51a of the septum 51 contacts closely with the convex surface 26s of the top part 26, there is almost no chance that the outer surface 51a of the septum 51 comes into contact with the liquid substance, which is different from the conventional configuration shown in FIG. 8D.

After stopping the passage of liquid between the male member 1 and the needle-less port 50, the male member 1 is pulled out from the needle-less port 50 from the state of FIG. 4C.

As described above, since the top edge 26e of the top part 26 is engaged with the opening edge 57e of the pressing plate 56, the head part 23 cannot be displaced with respect to the needle-less port 50. Therefore, the tubular member 10 moves relative to the septum 51 and the head part 23. In this process, the edge of the slit 52 slides on the outer peripheral surface of the tubular member 10, thereby removing the liquid substance adhering to the outer peripheral surface of the tubular member 10. Further, the outer peripheral wall 21 of the cover 20 extends.

Figure 5A:
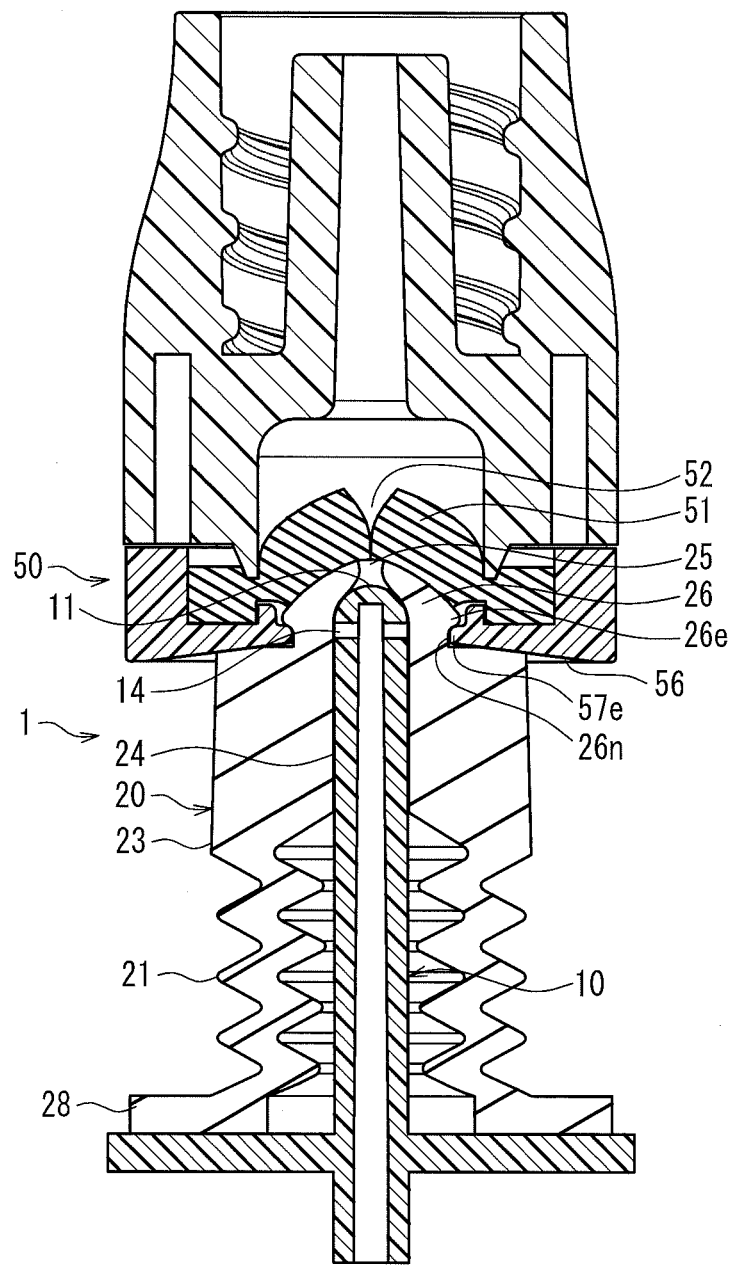
FIG. 5A is a cross-sectional view of the male member and the needle-less port during separation according to one embodiment of the present invention.

FIG. 5A is a cross-sectional view showing a state immediately after the tubular member 10 is pulled out from the slit 52 of the septum 51. The slit 52 of the septum 51 recovers elastically and closes as soon as the tubular member 10 is pulled out therefrom. The slit 25 opens slightly because the tip 11 of the tubular member 10 still remains in the slit 25 of the cover 20. The lateral hole 14 of the tubular member 10 is moved into the interior cavity 24 of the head part 23. The inner peripheral surface of the interior cavity 24 contacts closely with the outer peripheral surface of the tubular member 10, thereby blocking the lateral hole 14.

Figure 5B:
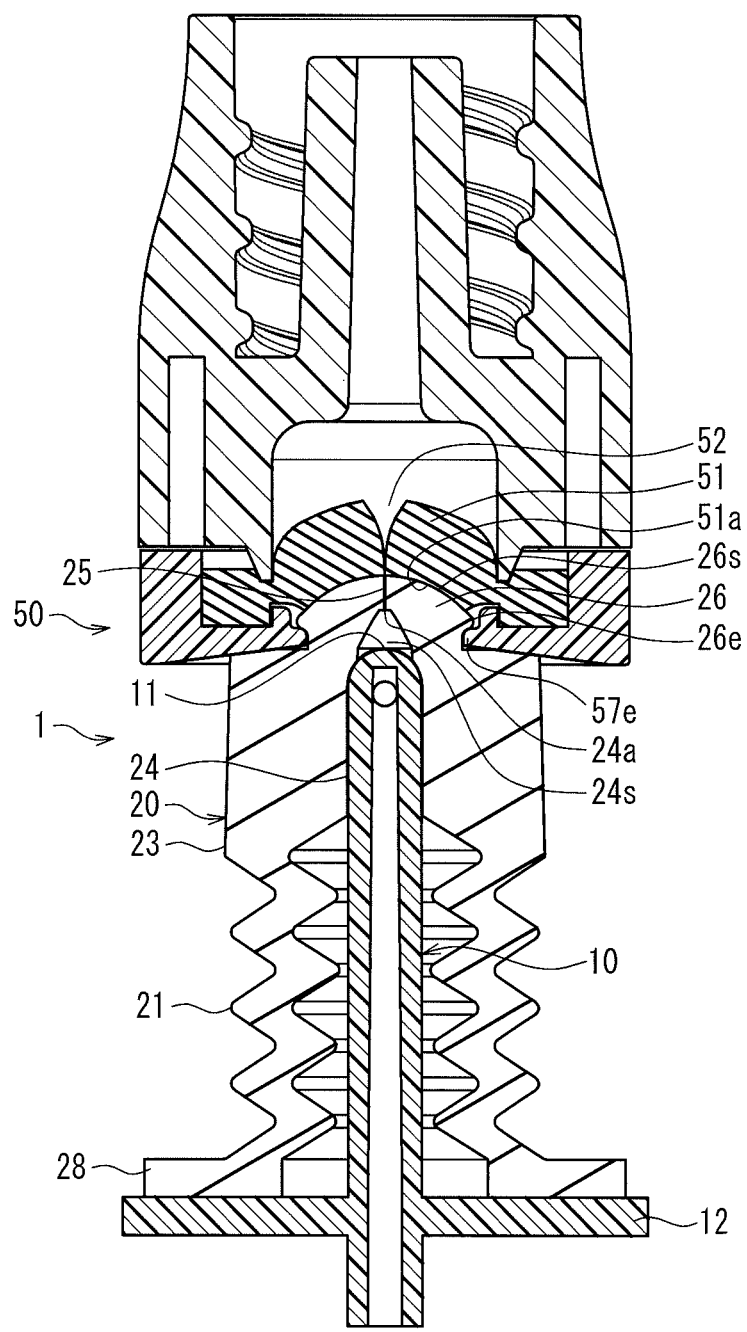
FIG. 5B is a cross-sectional view of the male member and the needle-less port during separation according to one embodiment of the present invention.

FIG. 5B is a cross-sectional view showing a state immediately after the tubular member 10 is pulled out from the slit 25 of the cover 20. Similarly to the slit 52 of the septum 51, the slit 25 of the cover 20 recovers elastically and closes as soon as the tubular member 10 is pulled out therefrom. Substantially in parallel to the closing of the slit 25, the tip 11 of the tubular member 10 is spaced apart from the innermost part 24a of the interior cavity 24, whereby the space 24s is formed. As described above, in the state of FIG. 5A, the slit 52 of the septum 51 is closed already and the inner peripheral surface of the interior cavity 24 contacts closely with the outer peripheral surface of the tubular member 10. Therefore, in the space 24s that is formed in the process of shifting from FIG. 5A to FIG. 5B, negative pressure is generated in accordance with the increase in the capacity of the space 24s. The negative pressure draws the liquid substance remaining between the outer surface 51a of the septum 51 and the convex surface 26s of the top part 26, into the space 24s via the slit 25.

Thereafter, when the male member 1 is pulled out further from the needle-less port 50, the engagement between the top edge 26e of the top part 26 and the opening edge 57e of the pressing plate 56 is released finally, and subsequently the convex surface 26s of the top part 26 and the outer surface 51a of the septum 51 are separated, thereby returning to the initial state shown in FIG. 4A.

As can be understood from the above description, according to the present embodiment, since negative pressure can be generated in the space 24s that is formed in the process of separating the male member 1 from the needle-less port 50, the liquid substance remaining in the vicinity of the slit 25 can be drawn into the space 24s via the slit 25. Consequently, it is possible to reduce the amount of the liquid substance adhering to the outer surface of the cover 20 of the male member 1 (i.e., the convex surface 26s) and the outer surface 51a of the septum 51 of the needle-less port 50 after separation of the male member 1 and the needle-less port 50.

Further, since the convex surface 26s is formed on the top part 26, i.e., the tip of the head part 23, the convex surface 26s can contact closely with the outer surface 51a of the septum 51 when the male member 1 and the needle-less port 50 are connected. Therefore, it is possible to reduce further the amount of the liquid substance adhering to the convex surface 26s and the outer surface 51a after separation of the male member 1 and the needle-less port 50.

Moreover, in an unconnected state (see FIG. 4A) where the male member 1 is not connected to the needle-less port 50, since the inner peripheral surface of the interior cavity 24 of the cover 20 blocks the lateral hole 14 of the tubular member 10, and the slit 25 of the cover 20 is closed, the liquid substance does not leak from the male member 1 in the unconnected state.

When the male member 1 and the needle-less port 50 are connected, as explained using FIG. 4C, the top edge 26e of the top part 26 and the opening edge 57e of the pressing plate 56 are engaged with each other. Thereby, at the time of separating the male member 1 and the needle-less port 50 after the connection, it is possible to prevent the separation of the cover 20 and the needle-less port 50 before the tubular member 10 is taken out from the slit 25 of the cover 20. Therefore, it is possible to reduce further the amount of the liquid substance adhering to the convex surface 26s and the outer surface 51a after separation of the male member 1 and the needle-less port 50. Further, at the time of the separation of the male member 1 and the needle-less port 50, the outer peripheral wall 21 of the cover 20 can extend to the initial state reliably.

The above embodiment is merely illustrative. The present invention is not limited to the above embodiment, and can be changed appropriately.

Figure 6:
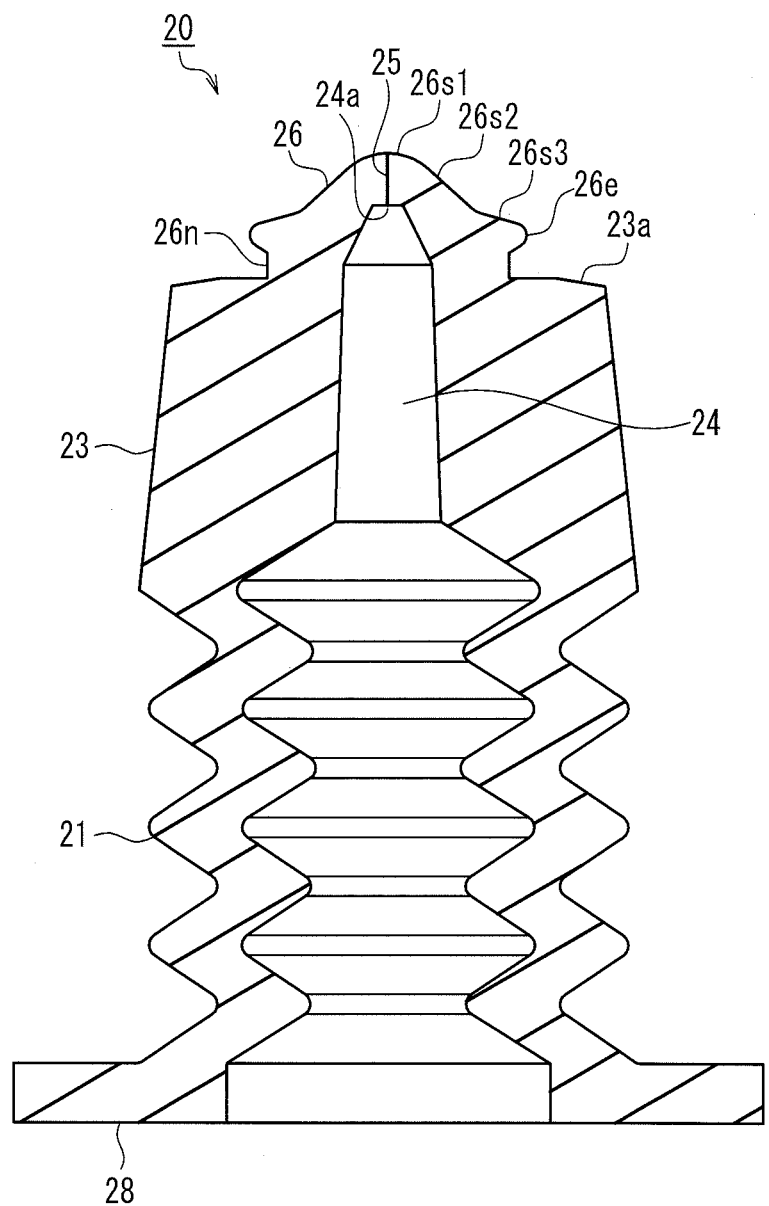
FIG. 6 is a cross-sectional view of a cover constituting a male member according to another embodiment of the present invention taken along a vertical direction.

In the above embodiment, on the surface of the top part 26 protruding from the upper surface 23a of the head part 23 on the side facing the female member (needle-less port 50), the substantially spherical convex surface 26s is formed. However, the shape of the outer surface of the top part 26 is not limited to this. FIG. 6 shows a cross-sectional view of another cover 20 constituting the male member of the present invention. On the surface of the top part 26 of the cover 20 on the side facing the female member, a spherical surface 26s1, a first circular truncated conical surface 26s2 and a second circular truncated conical surface 26s3 are arranged in this order from the center toward the top edge 26e. The slit 25 is formed in the spherical surface 26s1. A taper angle of the second circular truncated conical surface 26s3 is larger than a taper angle of the first circular truncated conical surface 26s2. The respective taper angles of the first circular truncated conical surface 26s2 and the second circular truncated conical surface 26s3 can be set at any angle.

In FIG. 6, a flat surface may be formed instead of the spherical surface 26s1. One circular conical surface may be formed instead of the spherical surface 26s1 and the first circular truncated conical surface 26s2. In this case, the slit 25 is formed in the middle of the circular conical surface. A ring-shaped flat surface may be formed outside the first circular truncated conical surface 26s2 instead of the second circular truncated conical surface 26s3. Alternatively, the second circular truncated conical surface 26s3 may be omitted. Alternatively, another one or more circular conical surfaces may be added further.

In the above description, "spherical surface", "circular truncated conical surface" and "circular conical surface" may include "substantially spherical surface", "substantially circular truncated conical surface" and "substantially circular conical surface", respectively, that are modification of the exact "spherical surface", "circular truncated conical surface" and "circular conical surface", respectively.

The top part 26 may have any surface shape other than the above. Generally, the surface of the top part 26 on the side facing the female member preferably is a convex surface that protrudes toward the female member, because such a surface shape improves adhesiveness with the outer surface of the female member (in the above embodiment, the outer surface 51a of the septum 51).

In the above embodiment, although the top part 26 is formed at the tip of the head part 23, it is possible to omit the top part 26. If the top part 26 is omitted, the outer surface of the cover and the outer surface of the female member (in the above embodiment, the outer surface 51a of the septum 51) may not contact closely with each other when the male member and the female member are connected. However, since negative pressure can be generated in the space 24s in the process of separating the male member and the female member, it is possible to reduce the amount of the liquid substance adhering to the outer surface of the cover and the outer surface of the female member after separation of the male member and the female member.

In the above embodiment, although the top edge 26e that is adjacent to the neck 26n is formed in the cover 20 as an engagement structure to be engaged with the female member, it is possible to omit the engagement structure. Also in this case, by appropriately setting an elastic force of the outer peripheral wall 21 of the cover 20, it is possible to realize a cover acting similarly to the cover of the above embodiment.

In order to maintain the connection state with the female member stably, the male member of the present invention may include an engagement member to be engaged with the female member. As such an engagement member, for example, a lock lever described in Patent Document 2 can be used.

Although the male member 1 of the above embodiment is a male luer that can be connected to the needle-less port equipped with the septum, the male member of the present invention can be connected to female members other than this. The configuration of the male member of the present invention can be changed appropriately depending on the configuration of the female member to be connected. For example, the male member of the present invention may be a bottle needle that can puncture a rubber stopper of a vial. In this case, it is preferable to carry out well-known changes in the male member, such as formation of a sharp tip to the tubular member 10, establishment of both a liquid flow path and a gas flow path that are independent from each other in the tubular member 10, and the like.

INDUSTRIAL APPLICABILITY

The use field of the present invention is not limited particularly, and the present invention can be used preferably for male members that are used in transport lines for the liquid transfusion, blood transfusion, extracorporeal circulation, etc. Further, the present invention can be used for male members of various kinds of connectors that are used at the time of preparing drug solutions and the like to be administered to patients. Particularly, the present invention can be used preferably in fields where hazardous drugs (e.g., antineoplastic agents) and the like that should be prevented from leakage and evaporation are handled. Moreover, the present invention can be used for male members that are used in various fields where liquid substances other than the medical use such as foods are handled.

DESCRIPTION OF REFERENCE NUMERALS 1 male member
10 tubular member
11 tip of tubular member
13 flow path of tubular member
14 lateral hole of tubular member
20 cover
21 outer peripheral wall
23 head part
24 interior cavity of head part
24a innermost part of interior cavity
24s space
25 slit
26 top part
26e top edge (engagement shape)
26s convex surface (spherical surface)
26s1 spherical surface
26s2 first circular truncated conical surface
26s3 second circular truncated conical surface
50 needle-less port (female member)
51 septum
51a outer surface of septum
52 slit of septum

The invention claimed is:

1. A male member, comprising:
a tubular member in which a flow path for carrying a liquid substance is formed; and
a cover that covers at least a tip of the tubular member,
wherein a lateral hole that communicates with the flow path is formed in an outer peripheral surface of the tubular member,
the cover includes an outer peripheral wall that can be deformed elastically by compression and a head part that is provided at one end of the outer peripheral wall,
the head part includes an interior cavity into which the tip of the tubular member is inserted,
a slit that penetrates the head part is formed in an innermost part of the interior cavity,
in a state where the outer peripheral wall is not deformed by compression, an inner peripheral surface of the interior cavity of the head part contacts closely with the outer peripheral surface of the tubular member so as to block the lateral hole, and the tip of the tubular member and the innermost part of the interior cavity are spaced apart from each other,
when the head part is displaced with respect to the tubular member so that the outer peripheral wall is deformed by compression, the tubular member penetrates the slit and the lateral hole is exposed from the head part, and
the head part has a convex surface formed on a side of the head part away from the outer peripheral wall with a slit formed in the convex surface.

2. The male member according to claim 1,
wherein a protruding top part is formed at a tip of the head part, and
the slit is formed in the top part.

3. The male member according to claim 2, wherein a surface of the top part on a side facing a female member includes a convex surface that protrudes toward the female member.

4. The male member according to claim 3, wherein the convex surface includes a spherical surface, a circular conical surface, or a circular truncated conical surface.

5. The male member according to claim 1, wherein an engagement shape that can be engaged with the female member is formed in the head part.

6. The male member according to claim 1, wherein, in the state where the outer peripheral wall is not deformed by compression, an airtight space is formed between the tip of the tubular member and the innermost part of the interior cavity.

* * * * *